(12) United States Patent
Calton et al.

(10) Patent No.: US 7,223,417 B2
(45) Date of Patent: May 29, 2007

(54) NUTRIENT FORMULATIONS

(76) Inventors: Gary J. Calton, 5331 Landing Rd., Elkridge, MD (US) 21075; Louis L. Wood, 11760 Gainsborough Rd., Rockville, MD (US) 20854

( * ) Notice: Subject to any disclaimer, the term of this patent is extended or adjusted under 35 U.S.C. 154(b) by 0 days.

(21) Appl. No.: 10/421,093

(22) Filed: Apr. 23, 2003

(65) Prior Publication Data

US 2003/0185876 A1    Oct. 2, 2003

Related U.S. Application Data

(63) Continuation of application No. 09/698,438, filed on Oct. 27, 2000, now abandoned.

(51) Int. Cl.
*A61K 47/00* (2006.01)
*A61K 31/70* (2006.01)
*A23L 1/00* (2006.01)

(52) U.S. Cl. .......................... 424/439; 426/73; 514/25

(58) Field of Classification Search .............. 424/34.8, 424/439; 426/73; 514/25; 436/73
See application file for complete search history.

(56) References Cited

U.S. PATENT DOCUMENTS 4,678,676 A * 7/1987 Ishizuka et al. ............ 426/573
5,164,213 A * 11/1992 Bonkowski ................. 426/281
5,620,757 A * 4/1997 Ninomiya et al. ......... 428/34.8

OTHER PUBLICATIONS

USDA Nutrient Database for Standard Reference, Release 12, 1998, NDB No. 16120, soy milk.*

* cited by examiner

*Primary Examiner*—San-Ming Hui
(74) *Attorney, Agent, or Firm*—Beverly J. Artale, Esq.

(57) ABSTRACT

Nutrient formulations are provided having a high content of carrageenan and a low liquid content. The nutrient formulation also contains at least one nutritional and/or pharmaceutical component such as flavorings, sweeteners, amino acids, fruit solids, protein and carbohydrates. The formulations are produced by mixing at least one carrageenan at a minimum of 5% by weight, and the desired nutritional and/or pharmaceutical component with no more than 50% by weight of a liquid.

11 Claims, No Drawings

NUTRIENT FORMULATIONS

This is a continuation of application Ser. No. 09/698,438, filed Oct. 27, 2000 now abandoned.

TECHNICAL FIELD

The present invention relates to novel nutrient compositions and to methods of preparing the same. More particularly, the present invention relates to methods and formulations useful in weight reduction and the delivery of nutrient and pharmaceutical supplements, e.g. vitamins, proteins, amino acids, in humans.

BACKGROUND OF THE INVENTION

Maintaining a healthy diet is essential for good health. Individuals are encouraged to control calories, to avoid fats, to increase fiber intake, to take vitamins as supplements and to eat cruciferous vegetables and fruits for a balanced diet. Despite the substantial advertising of the advantages of certain foods, control of calories and the detrimental effects of ignoring the advice, the fact remains that a substantial portion of the population has an unbalanced diet and is susceptible to various diseases.

One of the most desirable aides for maintaining a healthy diet is a good tasting non-caloric snack. Advantageously, the snack would be in the form of a candy or bar having a low fat and sugar content and having incorporated therein certain beneficially substances (e.g. amino acids, proteins, protein fractions, antioxidants, vitamins, minerals, and pharmaceuticals) to promote improved health.

Recently, it has been suggested that certain amino acids, when used as supplements to a normal diet in relatively large doses, have salutary effects on cardiovascular health (Drexler et al., "Correction of endothelial dysfunction in coronary microcirculation of hypercholesterolaemic patients by L-arginine", Lancet, Vol. 338, (Dec. 21/28, 1991)), pages 8782–8783); kidney health (Walser et al., "Can renal replacement be deferred by a supplemented very low protein diet?" J. Am. Soc. Nephrol., Vol. 10(1), (January 1999), pages 110–6); immune function and wound healing (Barbul et al., "Arginine enhances wound healing and lymphocyte immune responses in humans", Surgery, Vol. 108(2),(August 1990), pages 331–6); weight control (Geliebter et al., "Oral L-histidine fails to reduce taste and smell acuity but induces anorexia and urinary zinc excretion", Am. J. Clin. Nutr., Vol. 34(1), (January 1981), pages 119–20); muscle tone (Elam et al., "Effects of arginine and ornithine on strength, lean body mass and urinary hydroxyproline in adult males", J. Sports Med. Phys. Fitness, Vol. 29(1), (March 1989), pages 52–6); and cholesterol level (Hurson et al., "Metabolic effects of arginine in a healthy elderly population", J. Parenter. Enteral Nutr., Vol. 91 (3), (May–June 1995), pages 227–30; Braverman, E R and Pfeiffer, C C, The Healing Nutrients Within: Facts, Findings and New Research on Amino Acids. Keats Publishing, Inc., New Canaan, Conn., 1987, pages 181–182). The doses are sufficiently large that one would need to take a large number of pills or a large volume of powder to achieve the desired therapeutic dosage level. Unfortunately, amino acids have an undesirable flavor and can readily react with a variety of other chemicals found in foods, particularly when combined at elevated temperatures.

Accordingly, there exists a need to develop food products containing nutritional supplements and/or pharmaceuticals in useful amounts, which food products are capable of being formulated into a bar or candy, are organoleptically acceptable and are useful in small quantities to provide the daily requirements of a desired supplement.

SUMMARY OF THE INVENTION

A food product has now been developed which provides a healthy combination of nutritional supplements and/or pharmaceuticals, such as amino acids, proteins, protein fractions, antioxidants, minerals and pharmaceuticals, especially pharmaceuticals containing an amine group in their structure, in an easy and effective manner. The food products have lower amount of liquids than nutrient food products previously disclosed and may be easily formed into a bar or candy. Food products in accordance with the present invention are safe and storage stable under normal conditions for extended periods of time. Advantageously, food products in accordance with the invention are useful to provide amino acids and proteins in pharmaceutically acceptable dosages in a bio-available and organoleptically acceptable form in humans.

The food product of the present invention comprises at least 5% by weight of a carrageenan and less than 50% by weight liquid. The food product also comprises at least one nutritional or pharmaceutical component. The liquid component may be a mixture of oils, water, and other edible liquids. The food product is produced by thoroughly mixing the carrageenan, the desired component and the liquid to form a food mixture. The mixture is thereafter easily shaped into bars, discs, strands or the like, using conventional methods.

Accordingly, an advantage of the present invention is to provide novel food products having nutritional supplements and/or pharmaceuticals in amounts sufficient to promote a healthy diet.

It is also an advantage of the present invention to provide novel food products which are capable of being formulated into a bar or candy, are organoleptically acceptable and are useful in small quantities to provide the daily requirements of the a desired nutritional and pharmaceutical component.

It is a further advantage of the present invention to provide a novel food product capable of delivery of amino acids and proteins in a pleasant tasting and bio-available form.

It is also an advantage of the present invention to provide a nutrient food product that can be easily ingested in humans, and which combines with ingested water to provide a filled feeling in an individual. This satisfaction of hunger due to ingestion of the food product can result in a weight loss if the caloric value of the food product is low. Carrageenan is especially valuable in this respect since it contributes no calories, being classified as a non-digestible, soluble, dietary fiber.

Yet another advantage of the present invention is to provide a food product capable of relieving constipation by providing a means to easily ingest non-digestible, dietary fiber which can have an effect on the movement of food through the bowel providing a soft stool which is easily voided.

Other aspects and advantages of the present invention will become apparent from the following description, taken in conjunction with the ensuing examples and claims.

DESCRIPTION OF THE SPECIFIC EMBODIMENTS

The food product of the invention comprises at least 5% by weight of a carrageenan and no more than 50% by weight of a liquid. The food product may also comprise at least one nutritional or pharmaceutical component in an effective nutritional or pharmaceutical acceptably amount.

Any carrageenan will be useful and is intended within the scope of the invention provided that it is compatible with the active and essential components of the food product. Suitable carrageenans include, but are not limited to, iota, kappa and lambda carrageenans and mixtures thereof In a more preferred embodiment the carrageenan is iota or kappa carrageenan. In a still more preferred embodiment the carrageenan is lambda carrageenan.

Carrageenans are sulfated carbohydrates which are obtained mainly from red algae by extraction in the presence of lime (see for instance U.S. Pat. No. 3,956,173). In addition, carrageenans are widely available from various commercial sources such as FMC Corp, Princeton, N.J. 08543 or Shemberg U.S.A., Inc, Searsport, Me. 04974.

Unless otherwise noted, the carrageenans used in accordance with the present invention are used in the form of their sodium, potassium, and calcium salts of the sulfate groups or mixtures thereof. It is, however, possible to use the carrageenans as their acid sulfate forms partially free of Na, K, and Ca ions. Increased concentrations of the acid sulfate forms of the carrageenans are obtained by exchanging the Na, K, and Ca ions with aqueous solutions of strong acids such as HCl, $HNO_3$, $H_2SO_4$ and the like.

The amount of the at least one carrageenan to be used in the food product, will always substantially exceed amounts heretofore used in food products as thickening and smoothing additives, e.g. typically, 0.03% to 0.04% for iota carrageenan in milk products (Shemberg Product Data Sheet, Benlacta S-100, Shemberg USA, Searsport, Me.); 0.1 to 0.2% for lambda carrageenan in milk products (Shemberg Product Data Sheet, Isovis CS-9314, Shemberg USA, Searsport, Me.); and 0.4 to 1% for kappa carrageenan in meat products (Liangel F, Colloides Naturels, Inc., Bridgeport, N.J.).

In general the amount of carrageen is at least 5% by weight of the total food product. Preferably, the food product has carrageenan present in at least 10% by weight, most preferably at least about 15% by weight, of the total food product. In one embodiment of the invention, the carrageenan is present in an amount ranging from about 5–50, preferably 10–45%, by weight of the food product.

The food product of this invention contains not more than 50% by weight of liquids. Preferably, the food product of the invention contains less than 50% by weight of liquids. More preferably, the food product of the invention contains from about 5 to about 50% by weight of liquids. Still more preferably, the food product of the invention contains from about 10 to about 45% by weight of liquids. Most preferably, the food product of the invention contains from about 10 to about 40% by weight of liquids. In practice the purpose of the liquid is to allow the mixture to retain its form once mixed. The liquids may be any liquid capable of being consumed by humans which will not interfere with the active ingredients of the food product and which lends cohesiveness to the product. Suitable liquids include, but are not limited to, water, alcohols, glycerol, glycerin, 1,2-propane diols and homologs thereof, oils, sorbitan fatty acid esters, polyoxyethlene sorbitan fatty acid esters, sucrose esters, polyglycerol fatty acid esters, polypropylene glycol and the like. Preferred liquids include water, glycerin and polypropylene glycol or mixtures thereof.

The food product of the invention includes at least one nutritional or pharmaceutical component or supplement in an amount sufficient to provide desired health benefits. In a preferred embodiment, the supplemental component includes at least one amino acid. Suitable amino acids include, but are not limited to, amino acids selected from the group consisting of glycine, L-alanine, L-arginine, L-aspartic acid, L-citrulline, L-cystine, L-glutamic acid, L-glutamine, L-histidine, hydroxymethionine, L-isoleucine, L-leucine, L-lysine, L-methionine, L-ornithine, L-phenylalanine, L-proline, L-serine, L-threonine, L-tryptophan, L-tyrosine, L-valine, creatine, carnitine and mixtures thereof. For treating kidney disease, a preferred amino acid of one or more amino acids selected from the group consisting of glycine, L-arginine, L-glutamine, L-histidine, hydroxymethionine, L-isoleucine, L-leucine, L-lysine, L-methionine, L-phenylalanine, L-threonine, L-tryptophan, L-tyrosine, L-valine. Typically, amino acids or mixtures thereof are incorporated into the food product at levels ranging from about 0.01 to about 75, preferably from about 1 to about 50%, by weight of the total food product.

Proteins may also be included as a nutritional or pharmaceutical component in the food product. Suitable proteins include, but are not limited to, protein hydrolysates, or protein extracts, such as obtained from soy, whey, casein, wheat, corn, and albumin. Typically, proteins are incorporated into the food product at levels ranging from about 0.01 to about 75, preferably from about 1 to about 50% by weight of the total food product.

The food product may also include as a nutritional or pharmaceutical component at least one carbohydrate (saccharide), often free of glucose as the monomer or oligomer, e.g. sucrose. The total amount of saccharides, normally hexasaccharides will be in the range of about 0.01 to about 30 weight %, usually in the range of about 1 to about 25 weight %. Saccharides of particular interest include maltitol, conveniently used as a syrup, fructose, conveniently used as a solid, honey, rice syrup, corn syrup, high fructose corn syrup, high maltose corn syrup, and the like. Maltitol, when present, will generally be present in from about 2 to about 25 weight %. Fructose, when present, will be in the range of about 2 to about 20 weight %. Mannitol may be substituted in whole or part for the other saccharides, particularly reduced saccharides. Glycerin may also be employed as a sweetener in minor amounts, generally less than about 5 weight %.

Other nutritional or pharmaceutical component which may be incorporated into the food product of the invention include vitamins and, if desired, minerals. The vitamins and minerals will generally be present in at least 1%, more usually at least about 10%, and up to 100% or higher, of the recommended daily dosage of the ingredient. Typically, vitamins and minerals are incorporated into the food product at levels ranging from about 0.001 to about 75%, preferably from about 0.1 to about 50%, by weight of the total food product.

Vitamins of particular interest are antioxidants. However, vitamins which may be incorporated into the food product of the invention include both antioxidant and non-antioxidant vitamins, such as vitamin A, $B_6$, and $B_{12}$, D, E, and K, thiamin, riboflavin, ascorbic acid, folic acid, niacinamide, pantothenic acid, biotin, coenzyme Q, carnitine and mixtures thereof.

Minerals of interest include calcium, iron, iodine, magnesium, zinc, selenium, copper, manganese, chromium, molybdenum, chloride, and mixtures thereof.

The food product of the invention may also contain minor ingredients such as, for example, lipids, malic acid, fiber for reduction of cholesterol, (e.g. oat fiber, vegetable powder, etc.), colorants (e.g. beet powder, annatto, carmine, caramel color, FD&C colors, etc.), flavoring (e.g. chocolate, fruit, vanilla, confectionary particles, almonds etc.), artificial sweeteners (e.g. acesulfam k, sucralose, aspartame, alitame, stevioside, etc.), and anti-staling agents such as surfactants.

Generally, such minor ingredients are present in the food products in an amount ranging in total from about 2 to 15 weight % and individually from about 0.5 to 7.5, preferably about 0.5 to 5, weight %, to provide flavor, texture and/or appearance. Where the minor ingredient are lipids, they will preferably be present in less than 10% by weight, and desirably will be primarily polyunsaturated, including omega-3 polyunsaturated lipids. Where the minor ingredient is fiber, it will preferably be present in a range of about 0 to about 10% by weight. Where the minor ingredient is flavoring, it will preferably be present in a range of about 0 to about 10% by weight.

In addition to the ingredients described hereinabove, other functional ingredients may be added to enhance flavor texture, appearance and as a processing aide. Such ingredients are usually present in amounts not to exceed 3 weight %, preferably not 2 weight %, of the total food product.

The food product of the invention may be prepared by mixing ingredients of the product using any conventional mixing technique and thereafter forming and shaping the mixture by extruding or molding into a desired shape.

In a preferred embodiment, the food product of the invention is prepared by thoroughly mixing the liquid with highly soluble ingredients, e.g. sweeteners, flavors, colorants, lipids, and the like. The resulting mixture is thereafter mixed with the remaining solid ingredients, e.g. the carrageenan, and the desired nutritional or pharmaceutical component. Desirably, vitamins and minerals components and, as appropriate, other minor ingredients, are pre-blended and added as a single mixture. The remaining ingredients may then be added followed by mixing and scraping, where after a brief scraping period, further mixing may be performed up to 5 minutes to ensure substantial homogeneity of the product. The mix is then extruded, formed, and packaged as desired.

The mixture may be easily shaped into bars, discs, strands or the like as desired. When used in the form of a bar, ingredients of particular interest, in addition to the specific amino acids previously described, are set forth in the following table:

TABLE

| Ingredient | Weight % range* |
| --- | --- |
| Carrageenan | 5–50 |
| Protein (total) | 0–35 |
| protein isolate | 0–50 |
| amino acid(s) | 0–50 |
| Carbohydrates | 0–30 |
| Maltitol syrup | 0–25 |
| Fructose, crystalline | 0–20 |
| Vitamins | 0–3 |
| Flavoring | 0–6 |
| Fiber | 0–10 |
| Liquid | 5–50 |

*When the weight % is 0, the ingredient is optionally present.

In order to further illustrate the present invention and the advantages thereof, the following specific examples are given. The examples are given as specific illustrations of the claimed invention. It should be understood, however, that the invention is not limited to the specific details set forth in the examples.

EXAMPLES

Example 1

Arginine, 25 g, was mixed with a mainly lambda carrageenan with minor amounts of kappa and iota carrageenans present, 25 g, and then flavorings were added, malic acid, 11 g, sucralose, 0.28 g (dry components 61.28 g), liquid apple flavor, 0.25 g (Otten, Philadelphia, Pa.) and 25 g of water, 8 g of glycerin and 4.75 g of 1,2-propane diol (liquid components 38 g) to obtain a food product having 38% liquid ingredients. These ingredients were mixed to a cohesive state using a kitchen mixer and then formed into bars weighing 13 g each. The result was a pleasant tasting food product.

Example 2

Arginine, 22 g, was mixed with mainly lambda carrageenan with minor amounts of kappa and iota carrageenans present, 22 g, and then flavorings were added, citric acid, 7 g, aspartame, 1 g, spray dried apple flavor, 13 g (Otten, Philadelphia, Pa.) (dry components 65 g), and 27 g of water and 2 g of glycerin (liquid components 29 g)) to obtain a food product having 31% liquid ingredients. These ingredients were mixed to a cohesive state using a commercial pasta mixer and then formed into bars. The result was a pleasant tasting food product.

Example 3

Carrageenan, mainly lambda carrageenan with minor amounts of kappa and iota carrageenans present, 50 g, was mixed with flavorings, citric acid, 7 g, aspartame, 1 g, spray dried apple flavor, 13 g (Otten, Philadelphia, Pa.) (dry components 71 g), and 27 g of water and 2 g of glycerin (liquid components 29 g)) to obtain a food product having 29% liquid ingredients. These ingredients were mixed to a cohesive state using a kitchen mixer and then formed into cylindrical bars by extrusion via an attachment to the mixer normally used for home sausage or pasta preparation. The result was a pleasant tasting food product.

Example 4

Carrageenan, mainly lambda carrageenan with minor amounts of kappa and iota carrageenans present, 1 g, was mixed with 1 g of a mixture of amino acids consisting of L-histidine, 7.97%; L-isoleucine, 10.14%; L-leucine, 15.94%; L-lysine, 11.59%; L-methionine, 15.94%; L-phenylalanine, 15.94%; L-threonine, 7.25%; L-tryptophan, 3.62%; and L-valine, 11.59%, with flavorings, malic acid, 0.15 g, aspartame, 0.04 g, spray dried strawberry flavor, 0.4 g (Craftmaster, Amityville, N.Y.) (dry components 2.19 g), and 2 g of water (liquid components 2 g) to obtain a food product having 48% liquid ingredients. These ingredients were mixed to a cohesive state by placing them in a bag and kneading thoroughly by hand and then formed into balls weighing approximately 3 g each. The result was a pleasant tasting food product.

Example 5

Arginine, 25 g, was mixed with a commercial carrageenan, mainly lambda carrageenan with minor amounts of kappa and iota carrageenans present, 25 g, and then flavorings were added, malic acid, 11 g, sucralose, 0.28 g) (dry components g), apple flavor, 0.25 g (Otten, Philadelphia, Pa.) and 25 g of water, 8 g of glycerin, 4.75 g of 1,2-propane diol and 3 g of vegetable oil water (liquid components 41 g) to obtain a food product having 40% liquid ingredients. These ingredients were mixed to a cohesive state using a pasta maker and then extruded as a ribbon and then cut into bars. The result was a pleasant tasting food product.

Example 6

The food product prepared in Example 3 was given as an aid in digestion. Persons taking the food product described it as pleasant. Their stools were softer and more frequent, thus increasing their health if they suffered from hemorrhoids or constipation.

Example 7

The food product prepared in Examples 1, 3 and 4 was given to patients as an aid in weight reduction. The patients were instructed to eat an amount equal to 5–15 g (total weight) between 10 minutes and 1 hour prior to their meal and then eat as desired. The patients reported a decline in total food intake and no hunger. The patients lost weight.

Example 8

The food product prepared in Example 1 and 4 was given to patients as a nutritional supplement to increase their protein intake. The product was found to have a pleasant mouth feel and taste and to give a burst of energy.

It is evident from the above results that the food product in accordance with the invention provides an easy, effective way to administer amino acids, reduce weight or avoid the results of constipation, in a pleasant desirable way at a therapeutic dose. The food product is attractive and enjoyable as a food supplement and is capable of augmenting the normal levels of the amino acids, proteins, vitamins and the like, in the human diet.

All publications and patent applications cited in this specification are herein incorporated by reference.

Although the foregoing invention has been described in some details by way of illustration and examples for purposes of clarity of understanding, it will be readily apparent to those of ordinary skill in the art in light of the teachings of this invention that certain changes and modifications may be made thereto without departing from the spirit or scope of the appended claims.

We claim:

1. A molded or extruded food product consisiting essentially of at least one carrageenan, at least one amino acid and from about 29% to about 50% by weight liquid, wherein said at least one carrageenen is present in at least 10% by weight of said food product, wherein said at least one amino acid is selected from the group consisting of arginine, histidine, glycine, L-alanine, L-arginine, L-aspartic acid, L-citrulline, L-cystine, L-glutamic acid, L-glutamine, L-histidine, hydroxymethionine, L-isoleucine, L-leucine, L-lysine, L-methionine, L-ornithine, L-phenylalamine, L-proline, L-serine, L-threonine, L-tryptophan, L-tyrosine, L-valine, creatine, carnitine and mixtures thereof, and wherein the food product is ingestible by humans and is formed by mixing the at least one carragen, the at least one amino acid and liquid to form a moldable or extrudable cohesive mixture and thereafter, molding or extruding the mixture into a desired form.

2. A food product according to claim 1 wherein said at least one carrageenan is present in an amount ranging from about 10 to about 45% by weight of said food product.

3. A food product according to claim 1, wherein said liquid is selected from the group consisting of water, alcohols, glycerin and 1,2-propane diols, sorbitan fatty acid esters, polyoxyethlene sorbitan fatty acid esters, sucrose esters, and polyglycerol fatty acid esters and mixtures.

4. A food product according to claim 1, wherein said amino acid is a mixture of branched chain amino acids.

5. A food product according to claim 1, wherein said amino acid is arginine.

6. A food product according to claim 1, wherein said amino acid is histidine.

7. A food product according to claim 1, wherein said amino acid consists of one or more amino acids selected from the group consisting of glycine, L-alanine, L-arginine, L-aspartic acid, L-citrulline, L-cystine, L-glutamic acid, L-glutamine, L-histidine, hydroxymethionine, L-isoleucine, L-leucine, L-lysine, L-methionine, L-ornithine, L-phenylalamine, L-proline, L-serine, L-threonine, L-tryptophan, L-tyrosine, L-valine, creatine, carnitine and mixtures thereof.

8. A food product according to claim 7, wherein said amino acid is a mixture of amino acids selected from the group consisting of glycine, L-glutamine, L-histidine, hydroxymethionine, L-isoleucine, L-leucine, L-lysine, L-methionine, L-phenylalamine, L-threonine, L-tryptophan, L-tyrosine, L-valine, and mixtures thereof.

9. A method for relieving constipation in humans comprising ingesting a food product according to claim 1.

10. A method for reducing weight in humans comprising ingesting a food product according to claim 1.

11. A food product according to claim 1 wherein the product is shaped in the form of a bar.

* * * * *